United States Patent [19]

Tseng et al.

[11] Patent Number: 5,614,583
[45] Date of Patent: Mar. 25, 1997

[54] HOMOGENIZED FLOWABLE HYDROGEL OF CROSSLINKED N-VINYL LACTAM POLYMER

[75] Inventors: Susan Y. Tseng, Staten Island, N.Y.; Jui-Chang Chuang, Wayne; Philip F. Wolf, Bridgewater, both of N.J.

[73] Assignee: ISP Investments Inc., Wilmington, Del.

[21] Appl. No.: 528,383

[22] Filed: Sep. 13, 1995

[51] Int. Cl.⁶ .............................. A61K 9/14; C08L 39/06
[52] U.S. Cl. .......................... 524/555; 424/486; 523/340; 523/346
[58] Field of Search ................................ 526/263, 264, 526/265

[56] References Cited

U.S. PATENT DOCUMENTS

| | | |
|---|---|---|
| 4,769,427 | 9/1988 | Nowakowsky et al. ............... 526/263 |
| 5,242,985 | 9/1993 | Shih et al. ............................... 526/264 |
| 5,283,305 | 2/1994 | Chuang et al. ......................... 526/263 |
| 5,439,950 | 8/1995 | Liao et al. .............................. 526/263 |

*Primary Examiner*—Peter F. Kulkosky
*Attorney, Agent, or Firm*—Marilyn J. Maue; Walter Katz; Joshua J. Ward

[57] ABSTRACT

This invention relates to a crosslinked N-vinyl lactam polymer in the form of a stable, homogenized flowable hydrogel having microparticles which can be passed through a screen of between about 40 and about 350 mesh size. The invention also concerns the process for the preparation of the homogenized gel and to its use as a hair and skin conditioner or as a carrier for a cosmetically or pharmaceutically active substance.

6 Claims, No Drawings

5,614,583

HOMOGENIZED FLOWABLE HYDROGEL OF CROSSLINKED N-VINYL LACTAM POLYMER

BACKGROUND OF THE INVENTION

Crosslinked vinylpyrrolidone polymeric powder has been prepared by rapid proliferous polymerization at high temperatures as described, for example, in U.S. Pat. No. 5,391,668. U.S. Pat. Nos. 5,089,910; 5,130,388 and 5,015,708 also describe processes for crosslinking vinyl lactam polymers to produce a powdery product. More recently, processes for free radical initiated polymerization and crosslinking of N-vinyl lactam monomers and comonomers have been developed which produce substantially solid formed or molded hydrogel products. These processes are described in U.S. Pat. Nos. 5,280,049; 5,362,796 and 5,354,823; however the products produced therein do not provide flowable hydrogels composed of micronized particles.

Accordingly, it is an object of the present invention to produce a crosslinked N-vinyl lactam polymer in a unique form such as a flowable micronized hydrogel suitable as a carrier for cosmetically and/or pharmaceutically active compounds in a cream, lotion or ointment formulation or as a moisturizer applied directly to the skin or hair.

Another object is to provide a liquid film for easily releasable wound dressings which extend the efficacy of the medicament over longer periods of treatment.

Still another object is to provide an economical and commercially feasible process for producing a crosslinked N-vinyl lactam polymer in a flowable, homogenized form composed of microparticles.

These and other objects of this invention will become apparent from the following description and disclosure.

THE INVENTION

The flowable micronized hydrogel product of this invention is achieved by (1) forming a uniform liquid mixture of
 (a) between about 10 and about 30 wt. % of a polymerizable reactant containing at least 55% N-vinyl lactam monomer;
 (b) between about 0.01 and about 5 wt. % crosslinking agent;
 (c) between about 60 and about 90 wt. % solvent and
 (d) between about 0.1 and about 5 wt. % of a free radical initiator having a decomposition temperature below the boiling point of said solvent;

(2) in the absence of agitation and in an inert atmosphere, heating the mixture to between about 50° and about 80° C. for a period of from about 1 to about 5 hours to begin polymerization without displacement of the solvent medium, and then raising the temperature to between about 100° and about 145° C. for an additional period of from about 0.5 to about 3 hours or until completion of the reaction;

(3) recovering the crosslinked polymer in the form of a rubbery intermediate and digesting said intermediate in water to extract and remove soluble monomer, linear polymer and other residuals in the aqueous phase;

(4) recovering a clear, formed, crosslinked N-vinyl lactam polymer as a hydrogel mass of from about 0.5 to about 15 wt. % solids, preferably from about 1 to about 10 wt. % solids, and (5) subjecting said hydrogel mass to high speed, high shear agitation with a mixing device having a mechanical stirrer operating at between about 5,000 and about 50,000 rpm, preferably at between about 7,000 and about 35,000 rpm, to homogenize the hydrogel mass and to form flowable hydrogel microparticles which can be pushed through a sieve having openings of between about 40 and about 350 mesh preferably between about 70 and about 150 mesh. The stirrer or propeller speed is important since, below 5000 rpm, microparticles are not formed within a reasonable time frame; whereas above 50,000 rpm excess heat is generated sufficient to evaporate solvent below 80% of the hydrogel and thus destroy its flowable property. Vigorous mixing is generally effected over a period of from about 15 minutes to about 1 hour, although longer mixing times can be employed without adverse effect. Particularly good agitation is achieved with a cascade mixer or with a mixer having a housed impeller which breaks up a hydrogel mass introduced through an inlet port and directs hydrogel particles through an outlet port.

Most desirably, the flowable hydrogel microparticles of the present invention recovered from the high speed mixer pass through a 70–150 mesh screen and the micronized gel has a Brookfield viscosity* of from about 10,000 to about 70,000 cps; although hydrogel viscosities as low as 7,000 cps up to about 90,000 are also considered within the scope of this invention.

*RV Model, #7 spindle, 20 rpm

The superior conditioning properties of instant flowable, homogenized hydrogel product is attributable in part to its ability to absorb atmospheric moisture and to minimize evaporation of moisture from the skin or hair during treatment. Hence, as a carrier for skin rejuvenants or hair bleaches and dyes, the epidermis or hair follicles are not damaged by irritation, dryness or brittleness. The microparticle size of the hydrogel contributes to its flowability and provides for intimate admixing with active cosmetic or pharmaceutical agents in formulations applied as stable creams, lotions, ointments and the like. For example, the stable, homogenized microhydrogels of the present invention, can be combined with antiseptic agents, e.g. PVP/I or PVP/peroxide, to provide sustained and gradual release of the disinfectant. The flowable property of the present product allows for superior penetration of a wound or wound dressing which extends use of the dressing and provides gradual release of the medicament over an extended period. Additionally, the film forming properties of the present water insoluble hydrogel permits formulation with water soluble complexes, e.g. PVP/I and PVP/$H_2O_2$ and other water soluble components, to form a water resistant coating. Further, the unformulated hydrogel product herein described can be employed directly to a porous substrate, e.g. skin, hair, leather, etc., as a moisturizer. These and other valuable properties will become known by reason of the following disclosure.

In addition to the use of the product in its flowable form, the homogenized hydrogel can be subjected to drying so as to provide a finely divided particulate solid readily redispersible in water. For example, the product can be subjected to freeze drying for a period of from about 2 to about 24 hours at a temperature of between about −85° C. and −40° C., preferably between −80° C. and about −60° C. for a period of from 5 to 10 hours, to produce a white, fine powder, which is beneficial in reducing the costs of shipping and handling. Alternative drying procedures include drum drying, belt drying and spray drying at 120° C. to about 140° C.

The micronized, homogenized hydrogel of this invention is derived from the homopolymerization or copolymerization of N-vinyl pyrrolidone and/or N-vinyl caprolactam which is between about 0.01 and about 5% crosslinked, preferably between about 0.1 and about 2% crosslinked, with a suitable polyfunctional crosslinking agent.

As indicated, the N-vinyl lactam monomer may be combined with a polymerizable comonomer, preferably in an amount not more than 30% comonomer. Suitable comonomers are those which are soluble in the reaction solvent and include olefinically unsaturated compounds such as another N-vinyl formamide, N-vinyl pyrrolidone, N-vinyl caprolactam, vinyl acetate, ammonium and alkali salts of acrylic acid and methacrylic acid, acrylamide, methacrylamide, lower alkyl acrylates or methacrylates, acrylonitrile, vinyl chloride, hydroxyalkyl acrylates or methacrylates, hydroxybutyl vinyl ether, quaternized dimethylamino lower alkyl acrylates or methacrylates and the like.

Representative of the crosslinking agents which can be employed are diallylimidazolidone; divinyl ether of diethylene glycol; pentaerythritol triallyl ether (PETE); triallyl-1,3,5-triazine-2,4,6-(1H,3H,5H)trione (TATT); ethylene glycol diacrylate; 2,4,6-triallyloxy-1,3,5-triazine; N-vinyl-3(E)-ethylidene pyrrolidone (EVP); 1,7-octadiene; 1,9-decadiene; divinyl benzene; methylenebis(methacrylamide); methylenebis(acrylamide); N,N-divinylimidazolidone; ethylene glycol diacrylate; ethylidene bis(N-vinyl pyrrolidone) (EBVP); etc.

Preferred products of this invention are those derived from N-vinyl pyrrolidone homopolymer or N-vinyl pyrrolidone/N-vinyl caprolactam copolymer which are crosslinked with EVP, EBVP or divinylimidazolidone. Most preferred is the EVP crosslinked N-vinyl pyrrolidone homopolymer.

The solvent used in the above polymer synthesis can be water, lower alkanol e.g. $C_1$ to $C_4$ alkanol, glycerol, or a mixture thereof; although pure, deionized water is preferred. The amount of solvent employed can vary over a wide range; however, between about 65% and 75% of the reaction mixture is usually sufficient to dissolve all reactive components. If desired, a small amount, e.g. between about 0.001 and about 1.0 wt. %, of a coloring agent can be added to the solvent or to the water wash.

Suitable polymerization initiators, more often employed in a concentration of from about 0.1 to about 3 wt. %, are free radical catalysts having 10 hours half life temperature and a decomposition temperature below the boiling point of the solvent employed. Such initiators include diacyl peroxides such as diacetyl peroxide, dibenzoyl peroxide, dilauroyl peroxide; peresters such as t-butylperoxy pivalate, t-butyl peroctoate, t-amylperoxy pivalate, t-butylperoxy-2-ethyl hexanolate; percarbonates such as dicyclo hexyl peroxy dicarbonate, as well as azo compounds such as 2,2'-azo-bis(isobutyrolnitrile), 2,2'-azo-bis(2,4-dimethyl-valeronitrite), 2,2'-azo-bis(cycanocyclohexane) and mixtures thereof; the organic peroxides being preferred.

The crosslinked gel, obtained after saturation in from about 5 to about 800 volumes of water for a period of from about 5 hours to about 2 days, contains between about 0.5 and 15 wt. % crosslinked polymer, between about 70 to 99.5 wt. % water and between about 0 to about 20 wt. % of an innocuous additive or a material which is chemically inactive in the polymerization, e.g. colorant, medicinal or other ingredients suitable for particular needs.

The present flowable hydrogel possesses many beneficial properties. For example, the present product maintains its original viscosity over a broad pH range, thus enabling formulation to a desired consistency with both acid and basic components. The active components can be those used in personal care and pharmaceutical applications. More specifically, the present products are valuable carriers in concentrations of from about 75 to about 99.9 wt. %, preferably from about 80 to about 93 wt. %, of the total composition containing an active component. Suitable active components include those employed in sun blocks; hair bleaches; depilation; skin depigmentation, rejuvenation, disinfection, moisturizing, softening and defoliantation. Since the present carriers are colorless and not irritating to the skin, they can be applied in formulations over a wound or employed in wound dressings without staining and without the customary stinging or burning sensation on the skin. The flowable hydrogels of this invention are more skin substantive than their non-flowable counterparts and prolong the efficacy of active components by forming a skin barrier which resists evaporation. As a dentifrice fixing agent, the flowable property of instant hydrogels permits better conformity with gums thus providing a more comfortable fit. These and many other uses of the present products will be suggested by the unique properties of the flowable hydrogels described herein.

Having generally described the invention, reference is now had to the following examples which illustrate preferred embodiments concerning the preparation and use of the present products, which examples are not to be construed as limiting to the scope of the invention as more broadly defined above and in the appended claims.

EXAMPLE 1

A homogeneous solution of 10.84 grams of N-vinyl pyrrolidone (VP), 0.0479 gram N-vinyl-3(E)-ethylidene pyrrolidone (EVP), 42.24 grams of distilled water and 0.1192 gram of tert-butylperoxy pivalate (LUPERSOL 11) was reacted under 25 mm Hg of nitrogen at 60° C. for 1.5 hours and then at 120° C. to 140° C. for 1.5 hours, after which the solution was allowed to cool to room temperature and the resulting rubbery product was then recovered and was introduced into about 800 volumes of distilled water and digested for 15 hours with simultaneous removal and replacement of the water until the mother liquor is free of residual monomer and soluble poly-(N-vinylpyrrolidone). During the above water digestion step, the rubbery product swelled to a clear, transparent hydrogel mass having a gel volume of 18 grams water per gram of crosslinked polymer. This hydrogel product, was then introduced into a Ross homogenizer where, at 7,000 rpm the hydrogel mass is reduced to flowable hydrogel having a Brookfield viscosity of 30,000 cps which hydrogel is composed of colorless, clear particles which pass through a 40 mesh screen.

EXAMPLE 2

Hydrogel products obtained from crosslinking the compositions shown in Table 1 for 1 hour at 70° C. followed by 2 hours at 100° C. and digested in 10 fold volumes of water over a period of 16 hours to remove contaminants, were recovered as a hydrogel mass having the indicated wt.% solids. These samples were separately homogenized in a Ross Homogenizer at room temperature operated 7,000 rpm for 30 minutes, after which the products, having the properties reported in Table 2, were recovered.

TABLE 1

| Sample | WEIGHT (GRAMS) | | | | | | |
|---|---|---|---|---|---|---|---|
| | A | B | C | D | E | F | G |
| VP | 39.84 | 39.93 | 49.8 | 39.92 | 11.95 | 9.543 | 319.04 |
| EVP Lupersol | 0.16 | 0.08 | 0.2 | 0.08 | 0.05 | 0.0454 | 0.96 |
| 554* | 0.398 | 0.4 | 0.73 | 0.336 | 0.12 | — | 3.35 |
| 11** | — | — | — | — | — | 0.51 | — |
| $H_2O$ | 160 | 160 | 200 | 160 | 48 | 90 | 1280 |
| % Solids in digested Hydrogel | 5.9 | 3 | 5 | 2.8 | 3 | 1.84 | 6.11 |

*tert-amylperoxy pivalate
**tert-butylperoxy pivalate

TABLE 2

| Sample | A | B | C | D | E | F | G |
|---|---|---|---|---|---|---|---|
| Particle Size thru Screen (Mesh) | 40 | 70 | 70 | 70 | 70 | 70 | 70 |
| % Solids in homogenized microhydrogel | 5.4 | 3 | 5 | 2.8 | 3 | 1.84 | 6.1 |
| Brookfield Viscosity (cps) | 34,000 | 15,000 to 25,000 | | | | . | 57,000 |

The products of the foregoing examples can be admixed at room temperature for 30 minutes with 0.05 wt. % of PVP/I disinfectant to provide a water insoluble creamy composition which can be applied as a thin film to a gauze pad for use as a wound dressing. Also, these hydrogel products can be mixed with an effective amount of a sun blocking agent or applied directly to the skin in a thin layer as a water insoluble moisturizer. Further, the present hydrogels can be employed as a stable carrier for standard concentrations of hair bleach, hair dye and hair straightening agents to minimize skin irritation and hair dryness or brittleness while imparting a silky, soft feel. Still further, the above products can be applied to leather for preservation and softening effects which qualities are enhanced by the hydrogel microparticle penetrating properties. Alternatively, about 0.5–5 wt. % of the present product can be added to a commercial liquid leather treating formulation, e.g. ARMOROL, to provide a nourishing cream which resists drying by exposure to sunlight.

Pharmaceutical applications for the homogenized hydrogel microparticles of the invention are also useful as a water barrier over cuts and burns or as a moisturizing carrier for antifungal or antiseptic creams and lotions such as those containing zinc oxide, hydrocortisone, sodium perborate, iodine, hydrogen iodide, oil of wintergreen, and the like.

When used in a formulation, the present hydrogel can replace all or a portion of the carrier normally employed in a cosmetic or pharmaceutical formulation. However, when used as the sole carrier, the composition generally contains between about 0.01 and about 15 wt. % of the active ingredient. These and other beneficial uses of the present flowable hydrogel products will become apparent and are within the scope of this invention.

The following examples describe the preparation of several cosmetic and pharmaceutical compositions.

EXAMPLE 3

The hydrogel of sample 1A was freeze-dried at −80° C. to form a powder. Into an 8 ounce jar, containing 2.5 g of the resulting crosslinked PVP powder was introduced, under gentle mixing conditions and at room temperature, 83.5 g of distilled water and 2.0 g of hydrogen peroxide (30%). After mixing for 5 minutes, the jar contents were refrigerated overnight after which the gel containing 0.69 wt. % $H_2O_2$ was removed as the product. Observation after 6 weeks showed the product to be stable. The distinfectant product of this example can be spread on the face as a treatment for acne.

EXAMPLE 4

An 8 ounce jar, containing 54.75 g of the flowable crosslinked PVP hydrogel of Sample 1A, is evaporated to a concentration of 36.5 g of hydrogel (8.1% solids) and 18.3 g of $H_2O_2$ (30% in distilled water) is then introduced with gentle mixing at ambient temperature for 10 minutes. The jar contents is refrigerated overnight and the resulting product contained 10% $H_2O_2$. This product can be applied to the hair as a bleach without scalp irritation.

EXAMPLE 5

Example 4 was repeated except that 0.30 g of lactic acid (88% aqueous solution) was substituted for 18.3 g $H_2O_2$. The pH of the refrigerated product, containing 0.5 wt. % lactic acid, was 3. The product was stable when inspected after 6 weeks storage. This product is spread on the skin as a cream to effect decolorization of brownish spots.

EXAMPLE 6

Example 5 was repeated except that 81.25 g of the homogenized, flowable gel and 4.92 g of lactic acid were substituted. The refrigerated product contained 5 wt. % lactic acid and had a pH of 2. The product was found to be stable when ispected after 6 weeks. This product is useful as a skin bleach.

EXAMPLE 7

A 6.11% solids crosslinked PVP, flowable, homogenized hydrogel (80 g) containing 0.08 g of formic acid was sealed in a reactor and held at 50° C. Iodine crystals contained in a separate zone of the reactor, were vaporized and allowed to condense into the hydrogel/formic acid liquid mixture. When all of the crystals had been vaporized, the temperature of the reactor was raised to 85° C. and reaction continued for 2 hours after which no additional iodine vapor was given off and a flowable hydrogel PVP/I complex, containing 0.73% available iodine and an iodine/iodide ratio of 2:1, was formed and collected. This product can be spread over a wound to disinfect the injury without stinging. Alternatively, the product can be coated on a wound dressing and dried thereon for subsequent use.

What is claimed is:

1. The process for producing a hydrogel which comprises
   (1) forming a uniform liquid mixture of
      (a) between about 10 and about 30 wt. % of a polymerizable reactant containing 55% to 100% N-vinyl lactam monomer;
      (b) between about 0.01 and about 5 wt. % crosslinking agent;
      (c) between about 60 and about 90 wt. % solvent and
      (d) between about 0.1 and about 5 wt. % of a free radical initiator having a decomposition temperature below the boiling point of said solvent;

(2) in the absence of agitation and in an inert atmosphere, heating the mixture to between about 50° and about 80° C. for a period of from about 1 to about 5 hours to begin polymerization without displacement of the solvent medium, and then raising the temperature to between about 100° and about 145° C. for an additional period of from about 0.5 to about 3 hours or until completion of the reaction indicated by the absence of an exotherm;

(3) recovering the crosslinked polymer in the form of a rubbery intermediate and digesting said intermediate in water to extract and remove soluble monomer, linear polymer and other residuals in the aqueous phase;

(4) recovering a clear, formed, crosslinked N-vinyl lactam polymer as a hydrogel mass of from about 0.5 to about 15 wt. % solids;

(5) subjecting said hydrogel mass to high speed, high shear mechanical agitation in a stirring device operating at between about 5,000 and about 50,000 rpm to homogenize the hydrogel and to form flowable hydrogel microparticles which can be passed through a sieve having openings of between about 40 and about 350 mesh and (6) recovering the homogenized, micronized flowable hydrogel as the product of the process.

2. The process of claim 1 wherein the hydrogel mass is agitated with a mechanical stirrer operating at between about 7,000 and about 35,000 rpm.

3. The process of claim 1 wherein the flowable hydrogel is freeze dried to a microfine powder at a temperature of between about −85° and about −40° C. over a period of from about 2 to about 24 hours.

4. The process of claim 3 wherein the flowable hydrogel is freeze dried at a temperature of between about −80° and about −60° C. for a period of from about 5 to about 10 hours.

5. The process of claim 1 wherein the flowable hydrogel is dried at a temperature of from about 120° to about 140° C.

6. The homogenized, microparticulate, flowable, clear, water insoluble product of the process of one of claims 1 and 3.

* * * * *